United States Patent
Allen et al.

(10) Patent No.: US 10,247,657 B2
(45) Date of Patent: Apr. 2, 2019

(54) FIRE TUBE SCANNER AND METHOD OF USE

(71) Applicants: Derek Allen, Fairview, MT (US); Dillon Allen, Rigby, ID (US); David Allen, Rigby, ID (US)

(72) Inventors: Derek Allen, Fairview, MT (US); Dillon Allen, Rigby, ID (US); David Allen, Rigby, ID (US)

(73) Assignee: Allen Ventures, LLC, Rigby, ID (US)

( * ) Notice: Subject to any disclaimer, the term of this patent is extended or adjusted under 35 U.S.C. 154(b) by 13 days.

(21) Appl. No.: 15/794,182

(22) Filed: Oct. 26, 2017

(65) Prior Publication Data
US 2018/0321133 A1 Nov. 8, 2018

Related U.S. Application Data

(63) Continuation of application No. 15/586,490, filed on May 4, 2017, now abandoned.

(51) Int. Cl.
| | |
|---|---|
| *G01R 33/02* | (2006.01) |
| *G01N 17/04* | (2006.01) |
| *F28G 15/04* | (2006.01) |
| *F28F 27/00* | (2006.01) |
| *F28G 1/02* | (2006.01) |

(Continued)

(52) U.S. Cl.
CPC ............ *G01N 17/04* (2013.01); *F28F 27/00* (2013.01); *F28G 1/02* (2013.01); *F28G 15/04* (2013.01); *G01N 17/006* (2013.01); *G01N 27/83* (2013.01)

(58) Field of Classification Search
CPC ...... G01N 27/83; G01N 27/90; G01N 27/906; G01N 27/9013; G01N 27/9033; G01N 27/904; F16L 2101/30; G01R 33/02; G01R 33/07; G01R 33/09; G01R 33/58; G01R 33/64
USPC ......... 324/220, 559, 76.26, 76.28, 394, 404, 324/405, 406, 407, 250, 262, 253, 221, 324/242–245, 754.01, 754.07, 754.21, 324/755.01
See application file for complete search history.

(56) References Cited

U.S. PATENT DOCUMENTS

| | | |
|---|---|---|
| 3,299,349 A | 1/1967 | Tompkins et al. |
| 3,538,433 A | 11/1970 | Wood et al. |
| 4,555,665 A | 11/1985 | Stanley et al. |

(Continued)

FOREIGN PATENT DOCUMENTS

EP          2506003          10/2012

*Primary Examiner* — Patrick Assouad
*Assistant Examiner* — Taqi R Nasir
(74) *Attorney, Agent, or Firm* — Schmeiser, Olsen & Watts, LLP

(57) ABSTRACT

Disclosed is a scanner for scanning fire tubes in heater treaters. A scanner may include a curved body. The curved body having an outside of a curve and an inside of a curve. At least one magnet is coupled to the outside of the curve of the curved body. At least one sensor is coupled adjacent the at least one magnet on the outside of the curve of the curved body. A data transmitter is coupled to the at least one sensor. At least one wheel is coupled to an edge of the curved body. A distance measurer is coupled to the curved body. A hook coupler is coupled to the curved body. A method of using the scanner for scanning a fire tube includes placing the scanner in the tube and pushing/pulling the scanner up and down the tube around the entire circumference of the tube.

20 Claims, 14 Drawing Sheets

(51) Int. Cl.
*G01N 27/83* (2006.01)
*G01N 17/00* (2006.01)

(56) References Cited

U.S. PATENT DOCUMENTS

| | | | |
|---|---|---|---|
| 4,702,689 A * | 10/1987 | Schmidt | B29C 45/27 |
| | | | 264/328.15 |
| 4,702,692 A * | 10/1987 | Burns | F23L 13/06 |
| | | | 137/625.31 |
| 5,565,633 A * | 10/1996 | Wernicke | G01N 27/82 |
| | | | 324/220 |
| 5,565,663 A * | 10/1996 | Kossakowski | H01H 9/08 |
| | | | 200/17 R |
| 5,581,037 A | 12/1996 | Kwun et al. | |
| 5,619,136 A | 4/1997 | Drury | |
| 5,793,205 A | 8/1998 | Griffith et al. | |
| 5,864,232 A * | 1/1999 | Laursen | G01N 27/902 |
| | | | 324/220 |
| 5,878,783 A * | 3/1999 | Smart | F16L 55/28 |
| | | | 104/138.2 |
| 6,023,986 A * | 2/2000 | Smith | G01C 7/06 |
| | | | 324/220 |
| 6,100,684 A | 8/2000 | Ramaut | |
| 6,318,194 B1 | 11/2001 | Marvin et al. | |
| 6,502,452 B1 * | 1/2003 | Gill | F16L 55/132 |
| | | | 138/90 |
| 6,967,478 B2 | 11/2005 | Wayman et al. | |
| 7,019,520 B2 | 3/2006 | Kwun et al. | |
| 8,089,273 B2 | 1/2012 | Hoyt | |
| 8,341,996 B2 | 1/2013 | Hallfeldt et al. | |
| 9,389,201 B2 | 7/2016 | Lavoie et al. | |
| 2011/0089937 A1 * | 4/2011 | Petrosky | G01N 27/90 |
| | | | 324/220 |
| 2012/0253696 A1 | 10/2012 | Pearson et al. | |
| 2013/0187641 A1 * | 7/2013 | Singer | G01N 27/82 |
| | | | 324/220 |
| 2016/0231279 A1 * | 8/2016 | Hoyt | G01N 29/2412 |
| 2018/0267554 A1 * | 9/2018 | Loosararian | G05D 1/0274 |

* cited by examiner

FIRE TUBE SCANNER AND METHOD OF USE

CROSS REFERENCE TO RELATED APPLICATION[S]

This application is a continuation of U.S. patent application entitled "FIRE TUBE SCANNER AND METHOD OF USE," Ser. No. 15/586,490, filed May 4, 2017, the disclosure of which is hereby incorporated entirely herein by reference.

BACKGROUND OF THE INVENTION

Technical Field

This invention relates to a scanner for scanning the outside of a heater treater's fire tube from the inside of the tube in order to determine the condition of the tube.

State of the Art

In the oil and gas industry, it is necessary to separate oil from salt water and other unwanted contaminants prior to shipping the oil to a refinery. One of the devices used to separate oil from salt water and unwanted solids is a heater treater. At an oil field, the oil is pumped from the ground and directly into a heater treater. A heater treater uses heat, pressures and chemicals in order to separate unwanted fluids and materials from oil.

A heater treater is a tank containing a heat source. This heat source is contained in a tube called a fire tube.

A fire tube is a large u-shaped metal pipe that is placed in the heater treater and submerged in the oil and water mixture. Typically a fire tube is made from steel pipe ranging in diameter from 12 inches to 24 inches and has a length of 4 feet to 15 feet.

One end of the fire tube contains a heat source such as a burner with an open flame. The other end of the fire tube is connected to a chimney stack for venting exhaust. The fire tube prevents the flame or heating element from direct contact with the oil and water mixture.

Due to the fact that the fire tube is immersed in highly corrosive salt water, fire tubes tend to pit and corrode very quickly. Additionally, fire tubes are exposed to heat which accelerates this corrosion.

If a fire tube degrades too much, significant salt water spills, oil spills, fires or accidents may occur. Therefore, it is very important to replace fire tubes before they fail.

Presently there is no cost effective method of inspecting a fire tube for corrosion. In fact, the typical method used to determine the extent of damage to a fire tube is to remove the tube completely from the heater treater. This process has significant costs including lost product time. Additionally, this process has the potential to cause accidents and the like.

Removing the fire tube from the heater treater may also speed up the degradation process as the tube is exposed to oxygen which may increase corrosion.

While there are many methods and devices for inspecting piping, because of the very specific configuration of the fire tube in the heater treater, none of these methods or devices can be used.

Accordingly, an invention is needed to a safe and cost effective method for inspecting the fire tube while the tube remains in place inside the heater treater.

SUMMARY OF EMBODIMENTS

The present invention discloses a scanner for scanning a fire tube in a heater treater and a method of using the scanner.

Disclosed is a scanner for use in scanning a fire tube in a heater treater, the scanner may include a curved body, wherein the curved body has an outside of a curve and an inside of a curve. At least one magnet may be coupled to the outside of the curve of the curved body. At least one sensor may be coupled adjacent the at least one magnet on the outside of the curve of the curved body. A data transmitter may be coupled to the at least one sensor. At least one wheel may be coupled to an edge of the curved body. A distance measurer may also be coupled to the curved body. A hook coupler may be coupled to the curved body.

Alternate embodiments may include a scanner in combination with a fire tube including a scanner having a body curved to fit inside a fire tube. At least one magnet may be coupled to an outside of the body. At least one sensor may be coupled adjacent the at least one magnet. At least one wheel may be coupled to an edge of the body. At least one data transmitter may be coupled to the body. A pole may also be coupled to the body. A fire tube including a hollow cylindrical pipe having an inside surface and an outside surface. The outside surface of the hollow cylindrical pipe may be submerged in fluid. The hollow cylindrical pipe may be U shaped. The at least one magnet may couple the scanner to the inside surface of the hollow cylindrical pipe.

In some embodiments, a method of scanning a fire tube for corrosion may include, cleaning an inside of a fire tube; placing a scanner in the fire tube, wherein the scanner is curved to match a curve of the inside of the fire tube; and pushing and pulling the scanner around an interior circumference of the fire tube, wherein the scanner transmits data to a computer as the scanner is pushed and pulled in the fire tube. Next, the computer analyzes the data to determine defects in the fire tube. Finally, removing the scanner from the inside of the fire tube.

The foregoing and other features and advantages of the present invention will be apparent from the following more detailed description of the particular embodiments of the invention, as illustrated in the accompanying drawings.

DETAILED DESCRIPTION OF EMBODIMENTS OF THE INVENTION

Embodiments of this invention disclose a scanner for use in a fire tube in a heater treater and a method of using the scanner. In the gas and oil industry, heater treaters are used to separate oil from water and other contaminants. This is done by adding heat, pressure and chemicals to the mixture.

Directly after the oil is pumped from the ground, it is placed in a heater treater which is a large tank with a horseshoe or U-shaped pipe that passes through an end or side of the tank depending on the orientation of the heater treater itself. The U-shaped pipe is a fire tube which is used to heat the oil in the heater treater. The U-shaped pipe contains a heating element such as a burner which heats the air in the pipe. The heat is transferred from the pipe to the oil.

Due to the fact that the fire tube is submerged in a mixture of salt water and oil, fire tubes corrode and deteriorate very quickly.

The scanner in this invention is designed to be placed into a fire tube while it is still in position in a heater treater. The scanner scans the outside of the pipe from its location inside the pipe, looking for pits, corrosion and other defects.

The scanner uses magnetic flux technology which utilizes magnets and sensors to determine the deterioration of metal. The magnets create a magnetic field through the fire tube and the sensors sense any leakage from the magnetic field.

While the magnetic flux scanning technology is known in the art, the configuration and method of use disclosed herein is novel.

FIGS. 1-10 illustrate a scanner 10 for use in a fire tube. The scanner 10 includes a curved body 12 which is curved in order to match or closely approximate the curve of the interior of the fire tube. The curved body 12 is formed from a silicone type material that contains wiring and sensors. The silicone type material holds the wiring and sensors in position for use in scanning a specific diameter fire tube.

Figure 8:
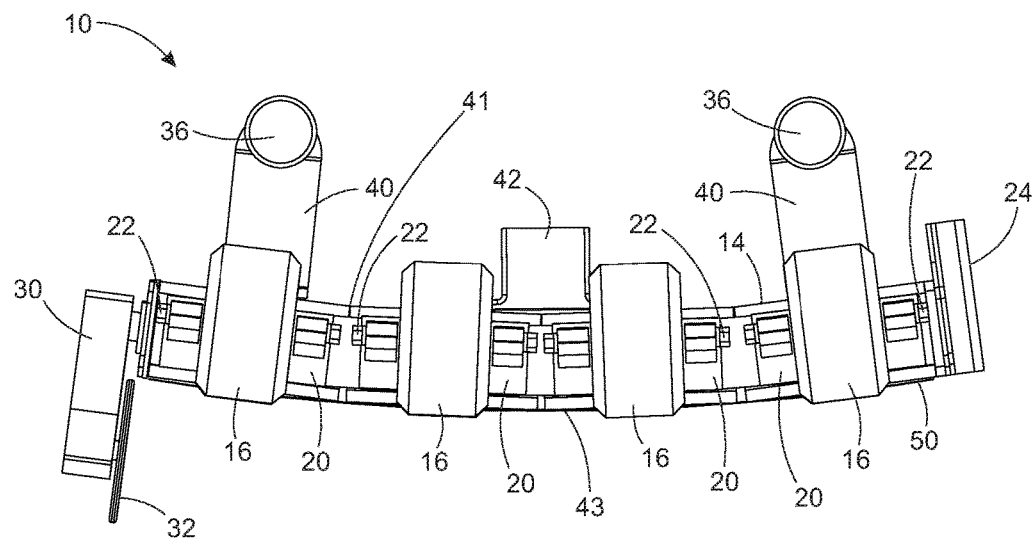
FIG. 8 is a front view of a scanner for use in a fire tube.
Figure 9:
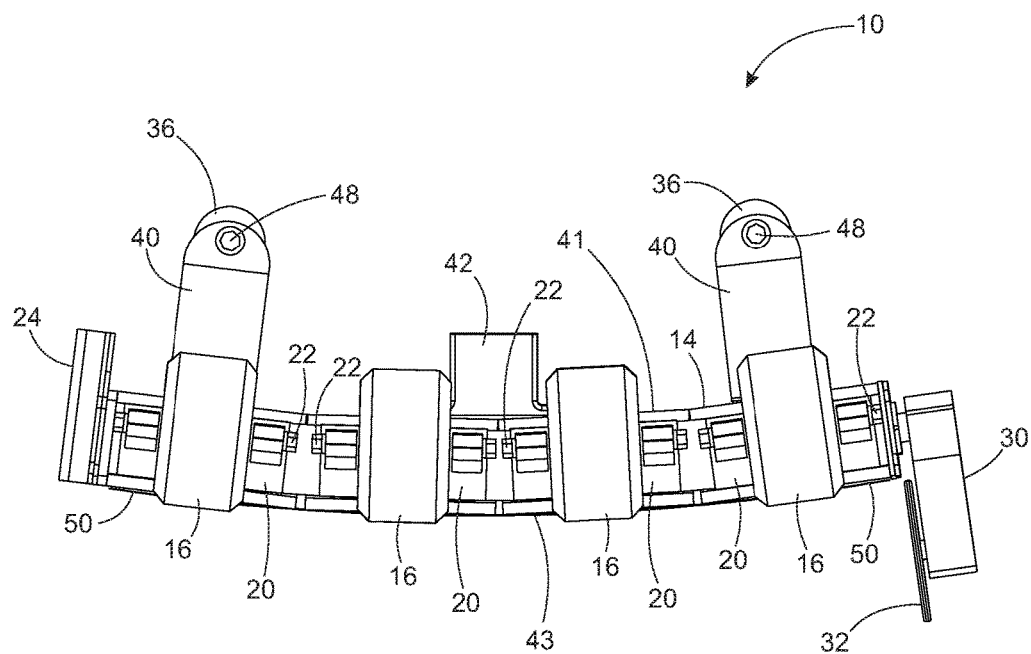
FIG. 9 is a back view of a scanner for use in a fire tube.

The top of the curved body 12 is the interior or inside of the curve 41 (see FIGS. 8-9), while the bottom of the curved body 12 is the exterior or outside of the curve 43 (see FIGS. 8-9). The curve of the curved body 12 is a portion of a circle with the inside of the curve 41 being the portion of the curve that would be the inside of the circle and the outside of the curve 43 being the portion of the curve that would be the outside of the circle. When the scanner 10 is being used in a fire tube, the inside of the curve 41 of the curved body 12 is the portion of the curved body 12 facing the interior of the tube while the outside of the curve 43 of the curved body 12 is the portion of the curved body 12 facing the tube wall.

The curved body 12 is illustrated as a thin rectangle in shape with the curve being along the long access of the rectangle.

While the curved body 12 is illustrated as a thin rectangle, the body 12 may be formed in any size or shape desired, provided the shape of the body 12 allows the curved body 12 to be placed adjacent the interior of the fire tube with the maximum possible surface area of the body 12 being next to the interior of the fire tube.

In alternate embodiments, the curved body 12 may be a smaller flat body that is small enough that the surface of the body may be adjacent the interior of the fire tube without the body being curved.

The top surface or interior of the curve 41 of the curved body 12 has a plurality of covers 14 coupled to it. The covers 14 are rectangular in shape and are used to cover and protect the top surface of the silicone type material containing the sensors. Additionally, the covers allow handles and the like to be coupled to the curved body 12.

While the covers 14 are illustrated as a plurality of rectangular covers, the covers 14 could be the same size and shape as the top surface of the curved body 12 or the like.

Wheels 16 are coupled to the proximal and distal, or front and back of the scanner 10. The wheels 16 support the curved body 12 and allow the curved body 12 to be moved along the interior surface of the fire tube.

The wheels 16, as illustrated, may be multiple wheels 16 mounted on both the front and back of the scanner 10. In the illustrations, there are four wheels 16 mounted on both the front and the back of the scanner 10.

The wheels 16 are mounted so that they extend slightly below the bottom surface of the curved body 12, in order to prevent the curved body 12 getting damaged by the interior of the fire tube.

In alternate embodiments, there may be greater or less number of wheels 16 mounted on the scanner 10.

The wheels 16 may be any type of wheel 16 with the strength to support the curved body 12 during use of the scanner 10.

The wheels 16 are mounted on or coupled to the curved body 12 by a wheel mount 20. The wheel mount 20, as illustrated has a mounting plate which is coupled to the curved body 12. The mounting plate has two arms which extend from two sides of the mounting plate. Each of these arms has an opening formed near an end of the arm farthest from the mounting plate.

An axle 18 is placed through an opening in one of the arms, through an opening in the center of the wheel 16 and then through an opening in the other arm. The openings in the arms support the axle 18 which in turn holds the wheel 16 in place.

The axle 18, as illustrated, is a long, thin, cylindrical member around which the wheel 16 rotates.

The ends of the axle 18 are held in place by axle couplers 22. Axle couplers 22 may be anything that stops the axle 18 from sliding from the openings in the arms of the wheel mount 20.

The axle couplers 22 may be nuts, pins, glue or the like. Additionally, the axle couplers 22 may simply be a widening of the axle 18 after it passes through the openings in the arms.

Two handles 36 are coupled to the top surface of the curved body 12. The two handles 36 are illustrated as two cylindrical members oriented parallel to the top surface of the curved body 12.

The handles 36 allow the user to pick up and move the scanner 10 without damaging any of the other pieces on the scanner 10.

The handles 36, though illustrated as cylindrical members, may be formed in any size or shape desired. The handles 36 may have a curved surface such as a contoured grip for comfort. The handles 36 may be curved as a whole in order to prevent the user's hands from slipping off the handle 36.

The handles 36 may also have a smooth surface such as a smooth metal handle, or the handles 36 may have a textured rubber surface in order to increase the grip on the handles 36. The handles 36 may also have a textured metal surface, a smooth rubber surface, or the like.

Though illustrated as having two handles 36, the scanner 10 may have more or less handles 36 as desired.

The handles 36 are coupled to a handle arm 40. The handle arm 40 is an angled metal member which extends from the handle 36 to the handle mount 40 orients the handle 36 in a position parallel to the surface of the curved body 12.

The handle 36 is coupled to the handle arm 40 by the handle coupler 48. The handle coupler 48 may be a threaded member coupled to an end of the handle 36 and placed through an opening in the handle arm 40 with a nut or bolt placed on the end of the threaded member in order to couple the handle 36 to the handle arm 40.

Alternately, the handle coupler 48 may be glue, adhesive, welding, screws, bolts, fasteners and the like.

The handle arm 40 may be formed in any shape desired. Additionally, the handle arm 40 may be formed from any material which is strong enough to support the curved body 12 when the handle 36 is used to lift the scanner 10.

The handle mount 38 is coupled to the opposite end of the handle arm 40 from the handle 36 itself. The handle mount 38 is a rectangular or square metallic plate used to couple the handle 36 and handle arm 40 to the surface of the curved body 12.

The handle mount 38 is depicted as a small square or rectangular plate with openings formed in the plate to receive couplers such as screws, bolts, pins or the like. The openings in the handle mount 38 allow the handle mount 38 to be coupled to the surface of the curved body 12.

Though the pictures illustrate the handles 36 being mounted to the top of the curved body 12 though the use of a handle arm 40 and handle mount 38, the handles 36 may be coupled to the top of the curved body 12 in any way that holds the handles 36 in position and allows the handles 36 to be used to lift the scanner 10.

Additionally, the handles 36 may be mounted on any accessible surface of the scanner 10.

A hook coupler 42 is also mounted on the top of the curved body 10 and within the inside of the curve of the curved body 10. The hook coupler 42 allows the user to hook a hook or the like to the top of the scanner 10 in order to allow the user to move the scanner 10 from a distance.

The hook coupler 42, as illustrated, is a cube member with an opening 46 formed through the interior of the cube. The opening 46 allows a hook, chain, rope, wire, or other device to be coupled permanently or removably to the top of the curved body 12.

The hook coupler 42 may be a cube, an arch, a sphere, a circle or any other shape that would be capable of having an opening 46 formed through its interior and of being mounted to a surface.

The hook coupler 42 is coupled or mounted to the top of the curved body 12 through the use of hook coupler mounts 44. Hook coupler mounts 44 are rectangular or square plates which are coupled to the lower side edges of the hook coupler 42.

The hook coupler mounts 44 have openings formed in them which receive couplers such as bolts, screws, pins or the like. The openings in the hook coupler mounts 44 allow the hook coupler mounts 44 to be securely fastened to the top of the curved body 12.

When the hook coupler mounts 44 are securely fastened to the top of the curved body 12, the hook coupler 42 is also securely mounted to the top of the curved body 12.

Though illustrated as being permanently mounted to the top of the curved body 12, the hook coupler 42 may also be removably mounted to the curved body 12.

In alternate embodiments, the hook coupler 42 may be mounted on any surface of the scanner 10 desired.

A data transmitter 24 is coupled to one side of the curved body 12 of the scanner 10. The data transmitter 24 acts to transmit data collected by the sensors on the scanner 10 to a computer 114 (see FIG. 17) at a different location.

Additionally, the data transmitter 24 receives power which powers the sensors on the scanner 10.

The data transmitter 24 has at least one port 28. The port 28 is configured to receive or mate with a cable 112 (see FIG. 17).

The port 28 may be any type of connection that allows data and power to be transmitted.

In embodiments of the present invention, multiple ports 28 may be used or a single port 28 may be sufficient to allow data and power to be transported.

The data transmitter 24 is coupled to the side of the curved body 12 through use of a data transmitter mounting plate 26. The data transmitter mounting plate 26 is coupled to the data transmitter 24. The data transmitter mounting plate 26 contains multiple holes or openings configured to receive fasteners such as screw, bolts, pins or the like. Fasteners are placed in the openings and used to secure the data transmitter mounting plate 26 to a side of the curved body 12.

In alternate embodiments, the data transmitter mounting plate 26 may be coupled to the curved body 12 through the use of adhesives, welding, or the like.

While illustrated as mounting to the side of the curved body 12, the data transmitter 24 may be mounted at any location desired provided the data transmitter 24 does not interfere with the functioning of the scanner 10.

A distance measurer 30 may be coupled to the opposite side of the scanner 10. The distance measurer 30 measures the distance that the scanner 10 moves along the interior of the fire tube. The distance the scanner 10 travels is transmitted to the computer.

The distance measurer 30 includes a wheel 32 which rolls along the surface of the fire tube as the scanner 10 is used. The distance measurer 30 uses the circumference of the wheel 32 and the number of times the wheel 32 rotates in order to calculate the distance the scanner 10 scans.

The distance measurer 30 is mounted to the curved body 12 by a distance measurer mounting plate 34. The distance measurer mounting plate 32 is a flat rectangular plate containing a plurality of openings. The distance measurer mounting plate 32 is coupled to the distance measurer 30. The openings in the distance measurer mounting plate 32 are for receiving screws, bolts, pins or other similar couplers. The couplers are placed through the holes in the distance measurer mounting plate 32 and then into the curved body 12 in order to secure the distance measurer 30 to the curved body 12.

In alternate embodiments of the distance measurer mounting plate 32, the distance measurer mounting plate 32 may be coupled to the curved body 12 through the use of welding, adhesives or the like.

Figure 1:
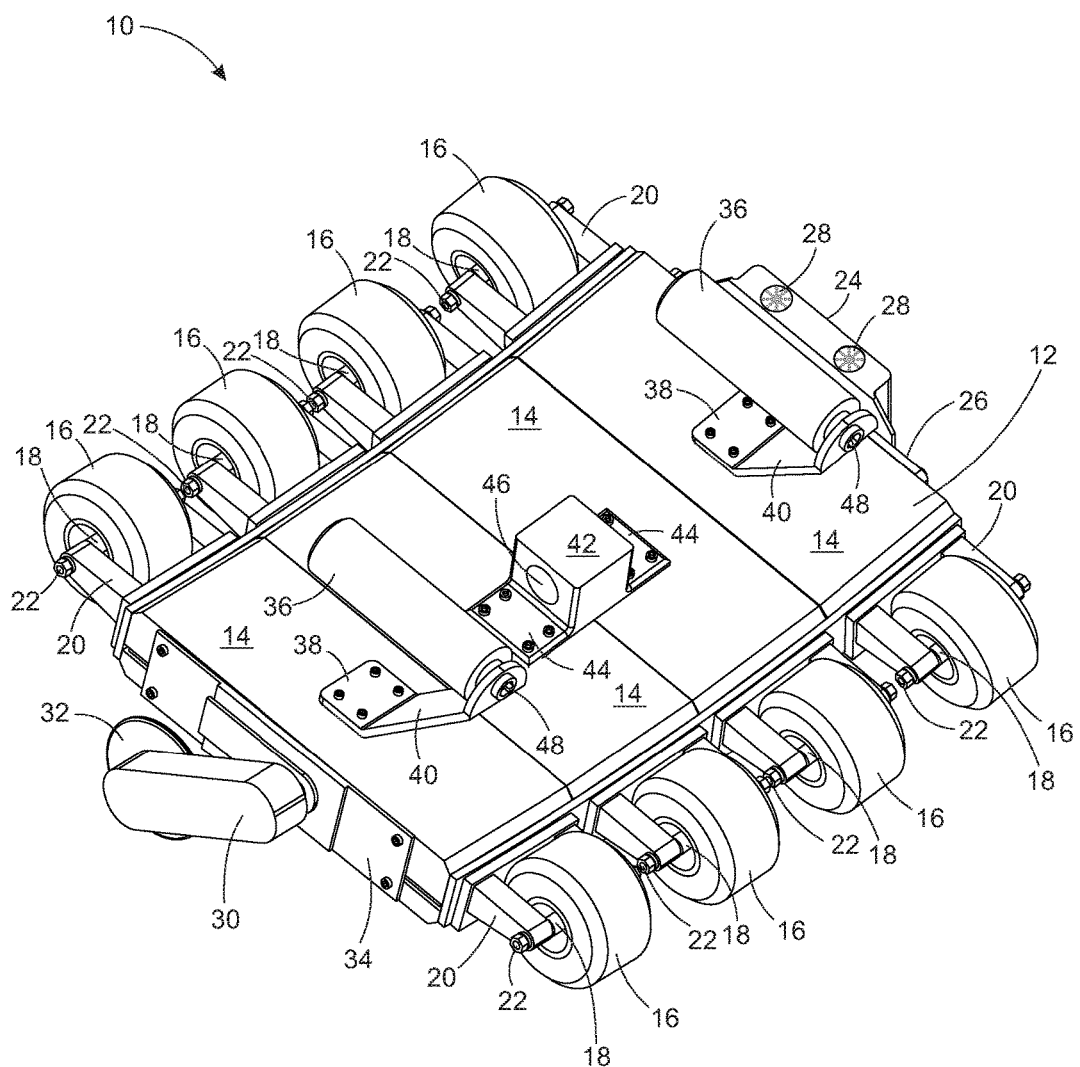
FIG. 1 is a top isometric left side view of a scanner for use in a fire tube.
Figure 2:
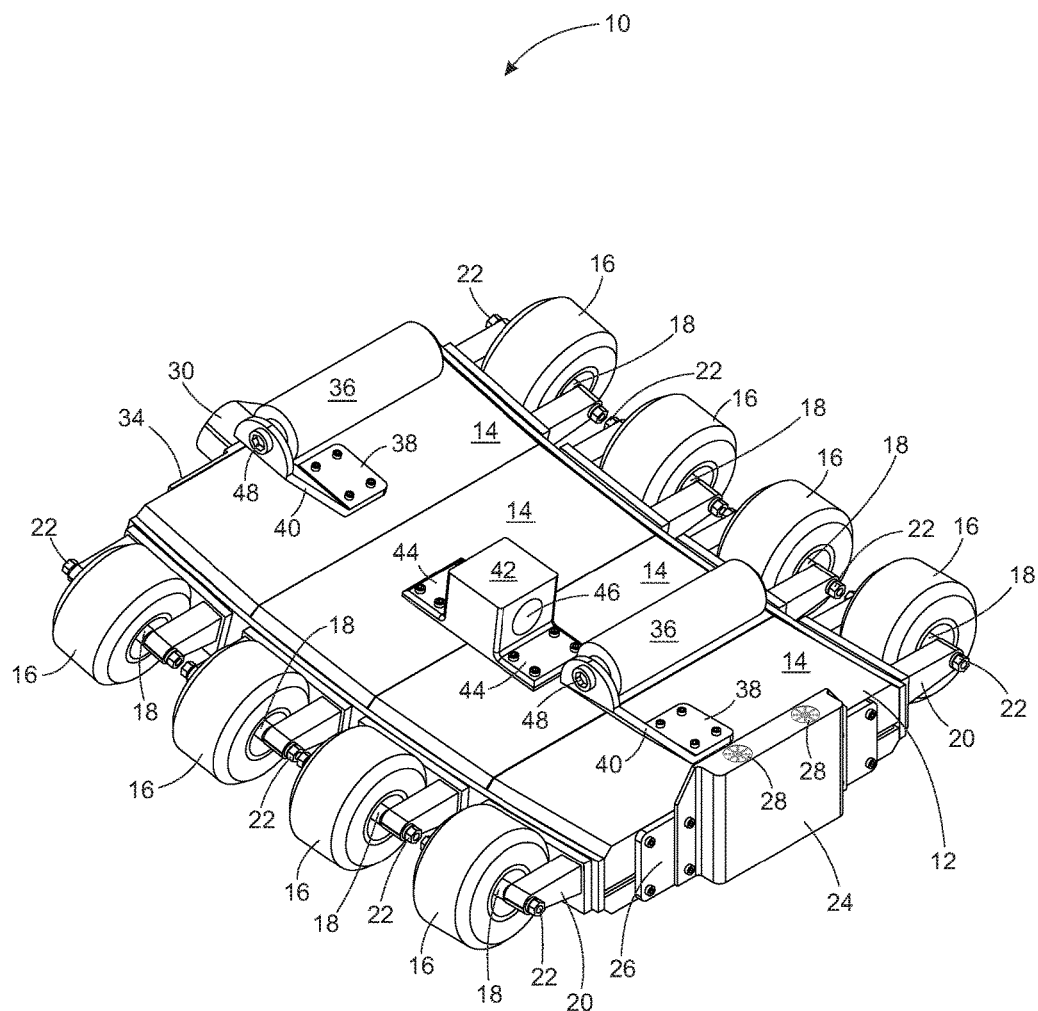
FIG. 2 is a top isometric right side view of a scanner for use in a fire tube.
Figure 3:
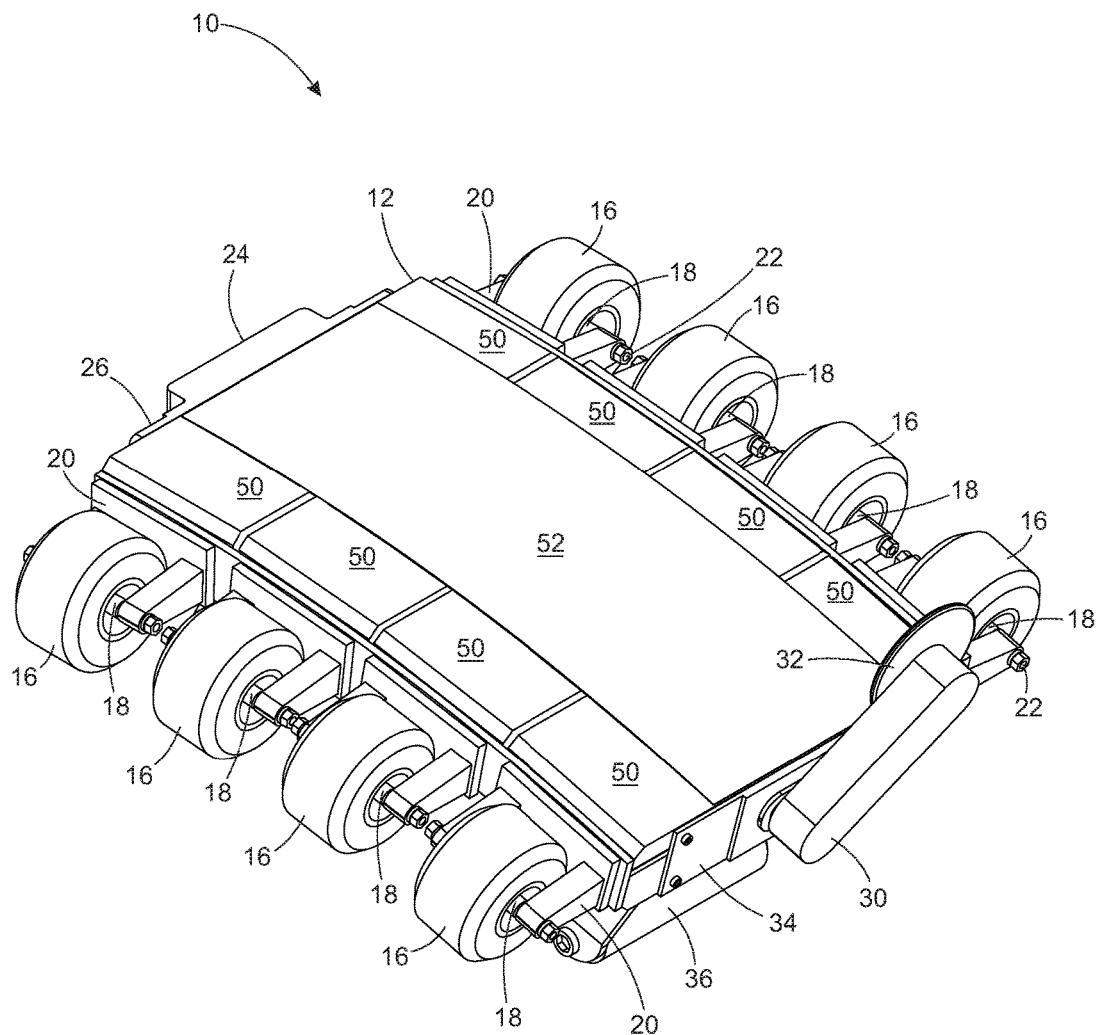
FIG. 3 is a bottom isometric view of a scanner for use in a fire tube.
Figure 4:
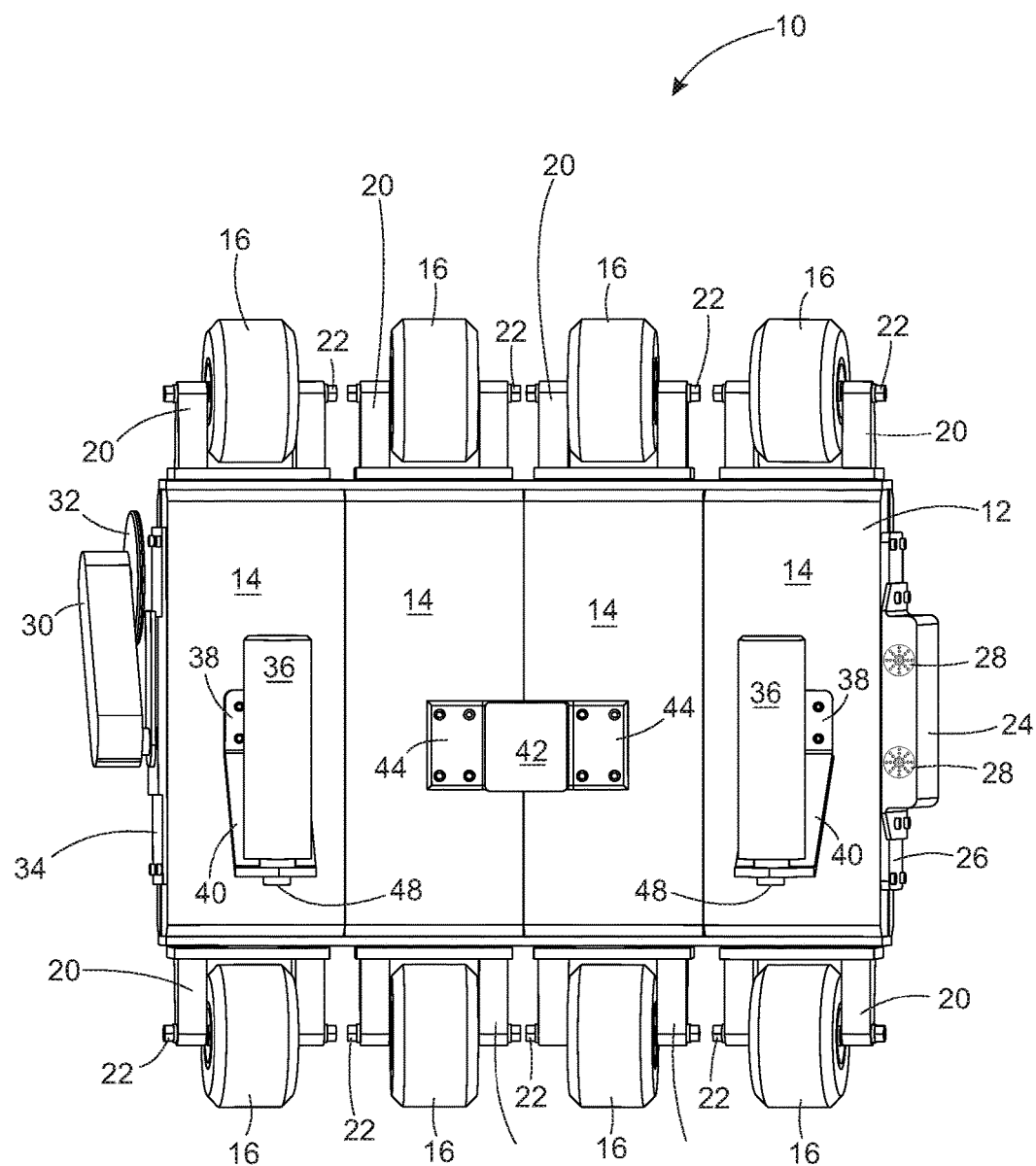
FIG. 4 is a top view of a scanner for use in a fire tube.
Figure 5:
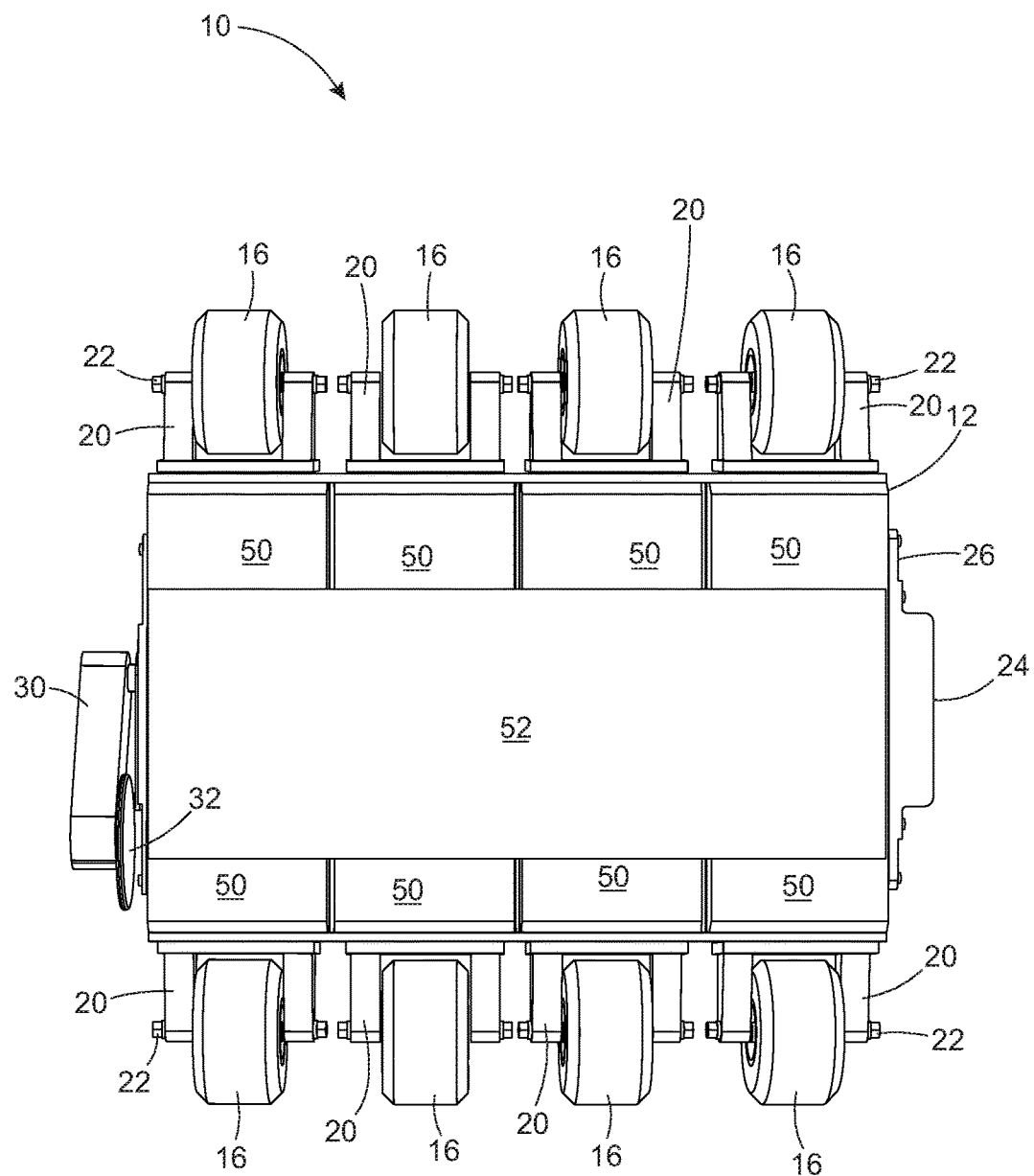
FIG. 5 is a bottom view of a scanner for use in a fire tube.
Figure 6:
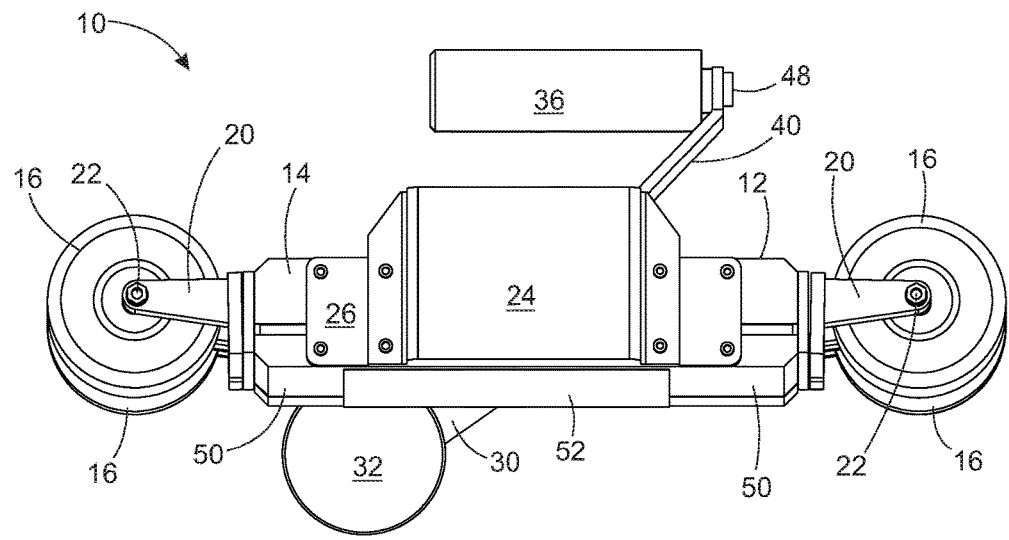
FIG. 6 is a right side view of a scanner for use in a fire tube.
Figure 7:
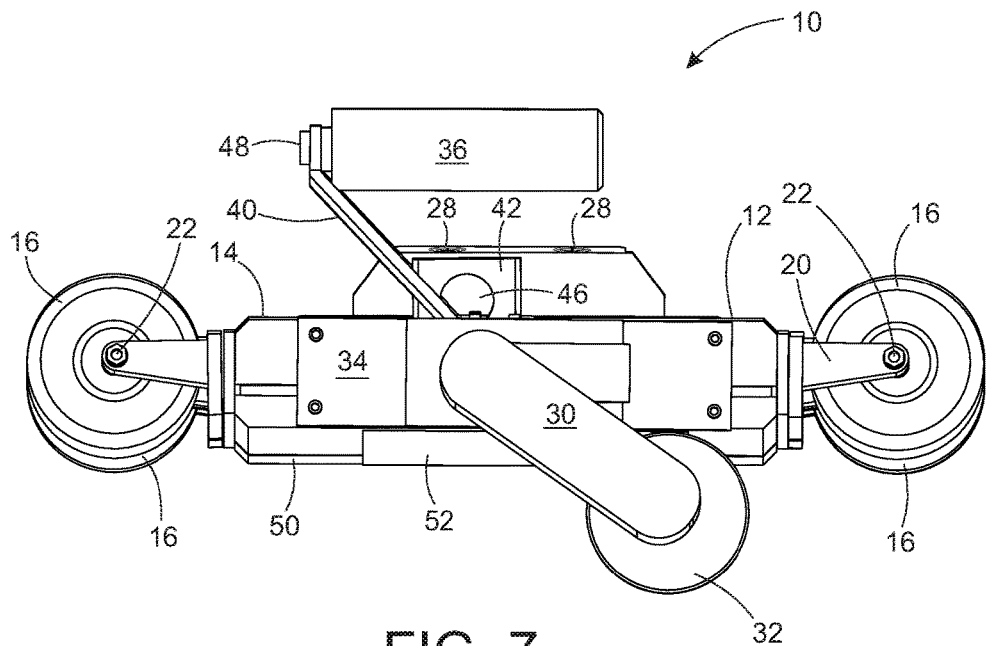
FIG. 7 is a left side view of a scanner for use in a fire tube.

FIG. 3 illustrates the bottom of the scanner 10. The bottom of the scanner 10 includes a plurality of magnets 50 coupled to the outside of the curve of the curved body 12.

The magnets 50 are illustrated as a plurality of individual magnets that abut the front and back edges of the curved body 12. In alternate embodiments, however, the magnets 50 may be one single magnet located at the front edge of the curved body 12.

Additionally, the magnets 50 may be a single magnet located at the front edge of the curved body 12 and the back edge of the curved body 12.

The magnets 50 may be any type of magnet that produces enough of a magnetic field to pass through the fire tube. The magnets 50 may be rare earth magnets, magnified metal, electro magnets or the like.

The magnets 50 also cause the scanner 10 to stick to the interior of the fire tube, which allows the scanner 10 to scan the entire circumference of the tube by sticking to the interior top, sides and other surfaces of the tube.

The magnets 50 may be oriented in any configuration that produces the best magnetic field for scanning the fire tube.

Between the two rows of magnets 50, is a sensor cover 52. The sensor cover or lid 52 acts as a skid plate and prevents the sensors from being damaged during the scanning process.

The sensor cover 52 is a thin, curved, rectangular member that covers the location of the sensors.

In alternate embodiments, the sensor cover 52 may be any size or shape necessary to protect the sensors.

Figure 10:
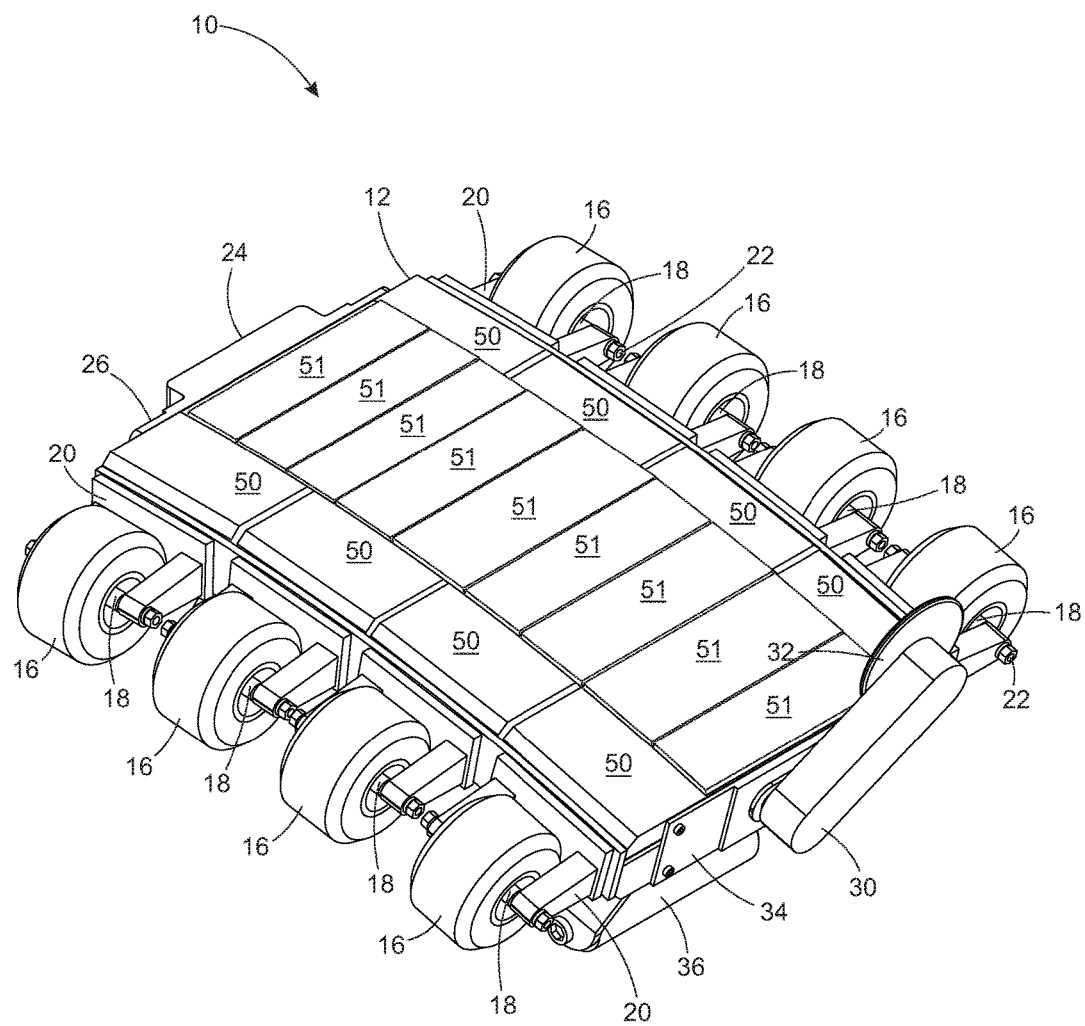
FIG. 10 is a bottom isometric view of a scanner for use in a fire tube with a sensor cover removed.

FIG. 10 illustrates the bottom of the scanner 10 with the sensor cover 52 removed leaving the sensors 51 visible. The sensors 51 are illustrated as rectangular boxes positioned in a row between the two rows of magnets 50.

The sensors 51 are held in place by the silicone type material that contains the sensors 51 and wiring for the scanner 10.

The sensors 51 may be any type of sensor that can detect changes in a magnetic field.

There may be one row of sensors 51 or multiple rows of sensors 51. Additionally, the sensors 51 may be configured in any orientation that allows them to best scan for changes in the magnetic field created by the magnets 50.

In additional embodiments, scanner 10 may also include a lever coupled to the curved body 12. The lever may be a bar that rotates about an axis at the top of the curved body 12. One end of the bar would be a handle, while the other end of the bar would apply force to the surface of the fire tube. When the user wants to remove the scanner 10 from the fire tube surface, the user pulls on the handle end of the lever. The other end of the lever is then forced down towards the surface of the fire tube. This acts as a lever to pry the magnets on the scanner 10 loose from the fire tube surface.

In alternate embodiments, the scanner 10 may use technology other than magnetic flux to scan the interior of the fire tube, i.e. ultrasound or the like.

Figure 11:
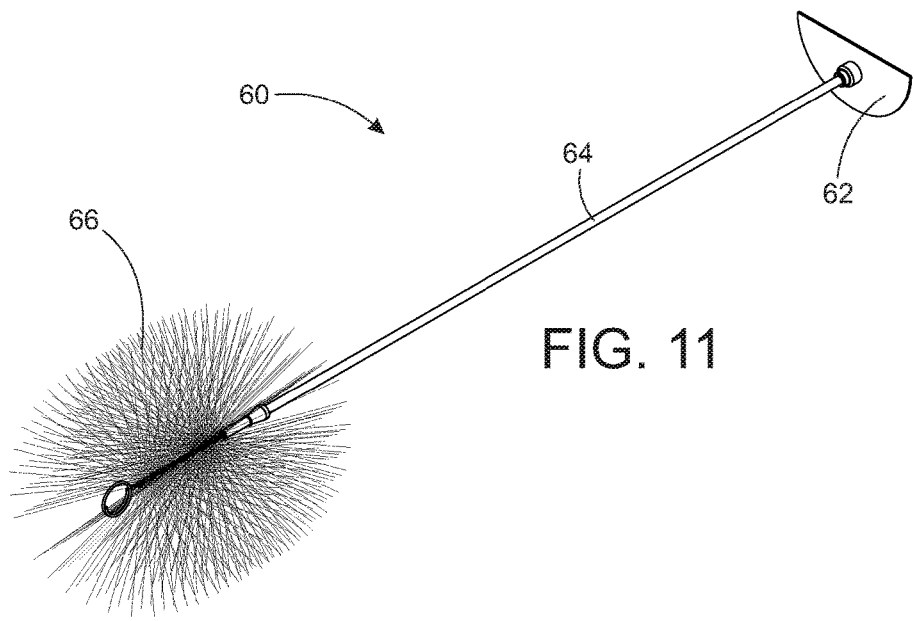
FIG. 11 is a left side isometric view of a brush for cleaning out a fire tube.
Figure 12:
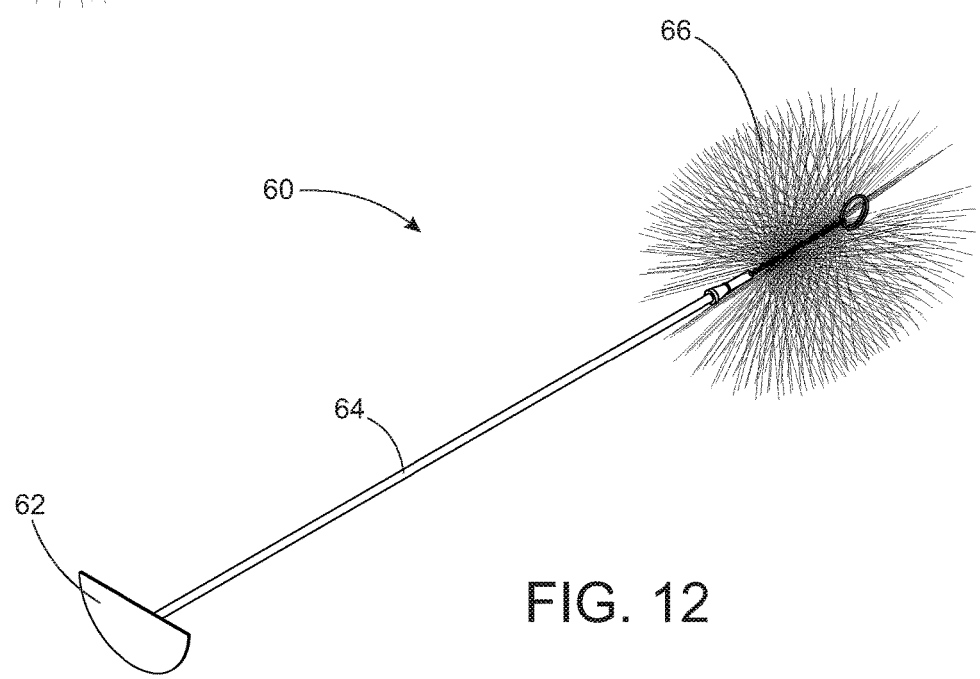
FIG. 12 is a right side isometric view of a brush for cleaning out a fire tube.

FIGS. 11-12 illustrated a brush 60 for cleaning the interior of the fire tube prior to scanning.

The brush 60 includes a round or cylindrical wire brush 66 coupled to the end of a rod 64. The wire brush 66 is sized to match the interior of the fire tube so that when the brush 60 is placed within the fire tube, the wire brush 66 abuts all of the surfaces of the interior of the fire tube at the same time.

The rod 64 may simply be a cylindrical rod of metal. Alternately, the rod 64 may telescope so as to allow the user to clean longer or shorter tubes.

The end of the rod 64 opposite the wire brush 66 has a handle 62 coupled to it. The handle 62 is formed as a half circle positioned with the diameter of the circle perpendicular to the rod 64. The half circle handle 62 gives the user plenty of leverage to manipulate the wire brush 66 located a distance from the user. The half circle shape allows the user to utilize both hands in order to twist the brush 60 as the wire brush 66 scrapes the inside of the surface of the fire tube.

The brush 60 may be rotated around the inside of the fire tube and pulled in and out of the fire tube when in use.

In alternate embodiments, the brush may be replaced with a scraper or other cleaning tool.

Figure 13:
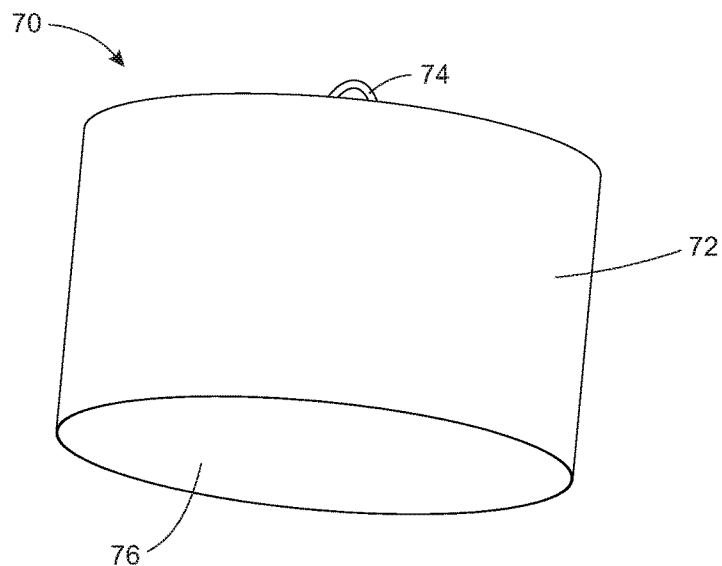
FIG. 13 is bottom isometric view of a plug for use in a fire tube during scanning.
Figure 14:
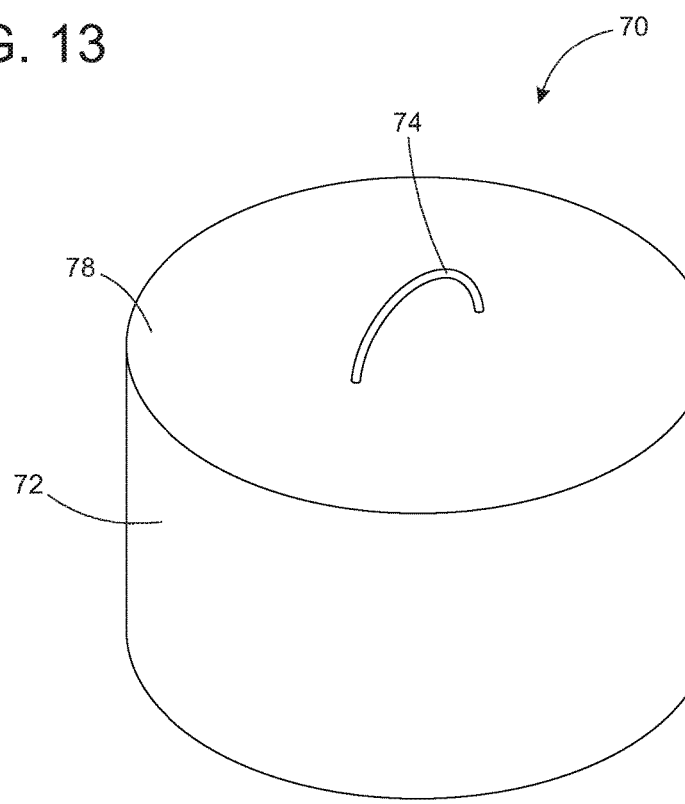
FIG. 14 is a top isometric view of a plug for use in a fire tube during scanning.

FIGS. 13-14 illustrated a plug 70 for use in the interior of the fire tube when the tube is being scanned. The plug 70 is a hollow cylindrical pipe 72 with a lid or cap 78 coupled to one end of the pipe 72 and an open end 76 at the other end. The hollow cylindrical pipe 72 is similar in diameter to the interior of the fire tube.

The plug 70 also includes an arched shape handle 74 coupled in the top center of the cap 78. The handle 74 is configured to be held by a hand or manipulated by a hook or the like. As illustrated the handle 74 is formed from an arched or C shaped metal rod.

In alternate embodiments, the handle 74 may be formed in any shape desired, including square, rectangular, U-shaped or the like.

The plug 70 is placed in the fire tube with the open end of the plug positioned towards the U-shaped bend in the fire tube. The plug 70 is then pushed until it abuts the turn in the fire tube (See FIG. 17).

The plug 70 prevents the scanner 10 from going too far into the fire tube and getting stuck in the bend.

In alternate embodiments of the present invention, the plug 70 could be replaced by an arm or stop that extends from the front of the scanner 10 and prevents the scanner from travelling too far into the fire tube.

Figure 15:
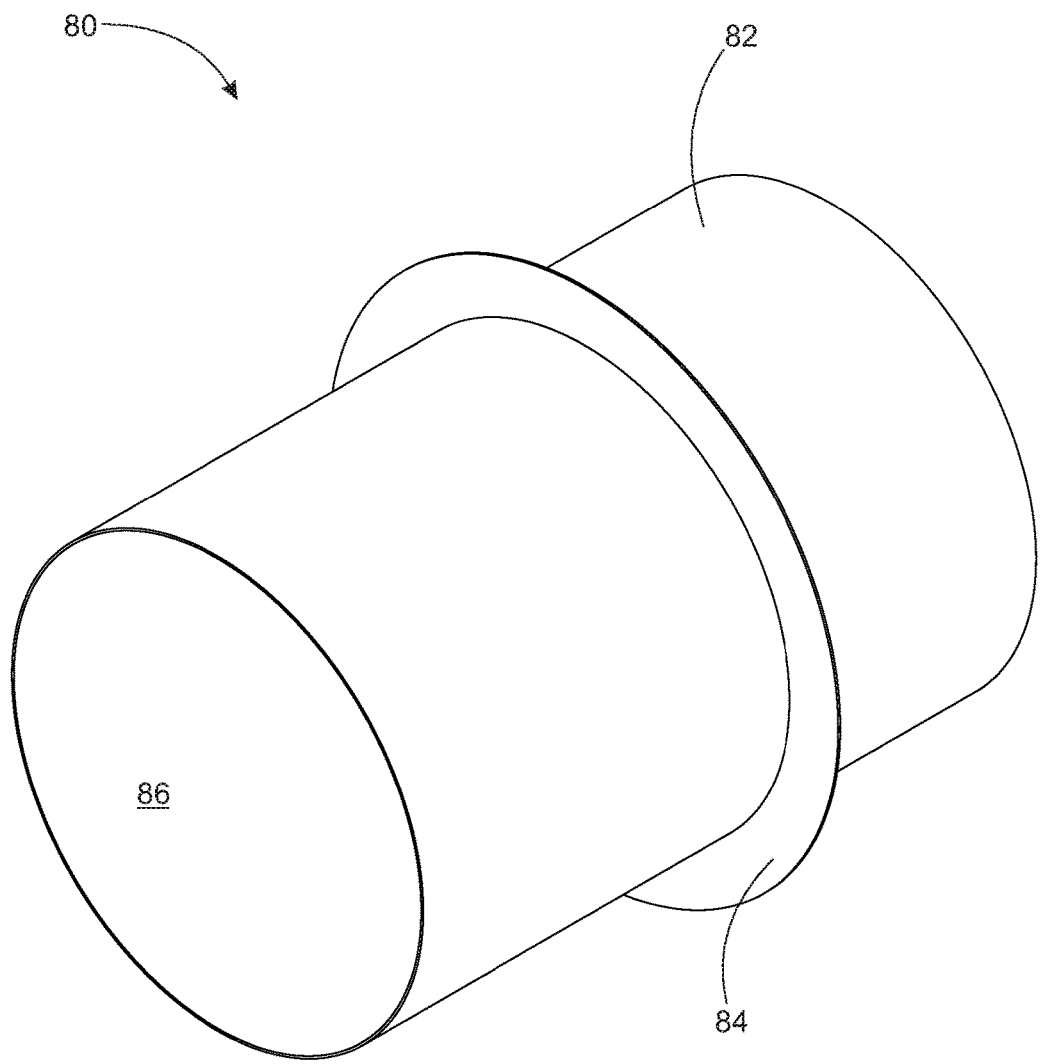
FIG. 15 is an isometric view of a collar for use in a fire tube during scanning.

FIG. 15 illustrates a collar 80 that is inserted in the open end of the fire tube during scanning. The collar 80 is a cylindrical tube 82 with open ends 86.

The collar 80 also includes a flange 84 that runs around the outer circumference of the collar 80. The flange 84 is a ring shaped member that extends from the surface of the collar 80 and prevents the collar 80 from being pushed too far into the fire tube.

When a fire tube is to be scanned the collar 80 is inserted into the open end of the fire tube (see FIG. 10). The collar 80 is formed from a non-magnetic material which the magnets on the scanner 10 will not stick to. The collar 80 acts as a way to get the scanner in and out of the fire tube.

When the scanner 10 is being inserted into the fire tube, the scanner 10 is placed on the collar 80 and then rolled into the fire tube. Alternately, when the scan of the fire tube has been completed, the scanner 10 can be rolled onto the collar 80 and then easily removed from the fire tube.

Figure 16:
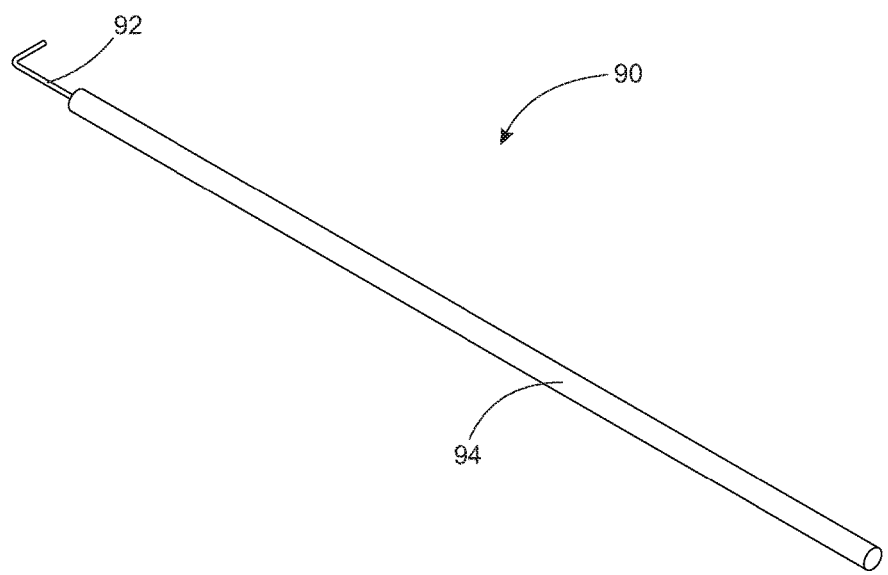
FIG. 16 is an isometric view of a pole for use in conjunction with a scanner in a fire tube.

FIG. 16 is an isometric view of a rod, pole or hook 90 for manipulating the scanner 10 and plug 70. The hook 90 includes a long cylindrical rod 94. The rod 94 may be formed from wood, metal, plastic, composites or the like. The rod 94 may be a solid cylinder or may include a handle location at a user end.

The rod 94 is coupled to hook 92. Hook 92 is a right angle hook formed from a smaller diameter rod. Hook 92 may be formed in any size or shape desired provided hook 92 is strong and shaped correctly to hook to and manipulate scanner 10 and plug 70.

Figure 17:
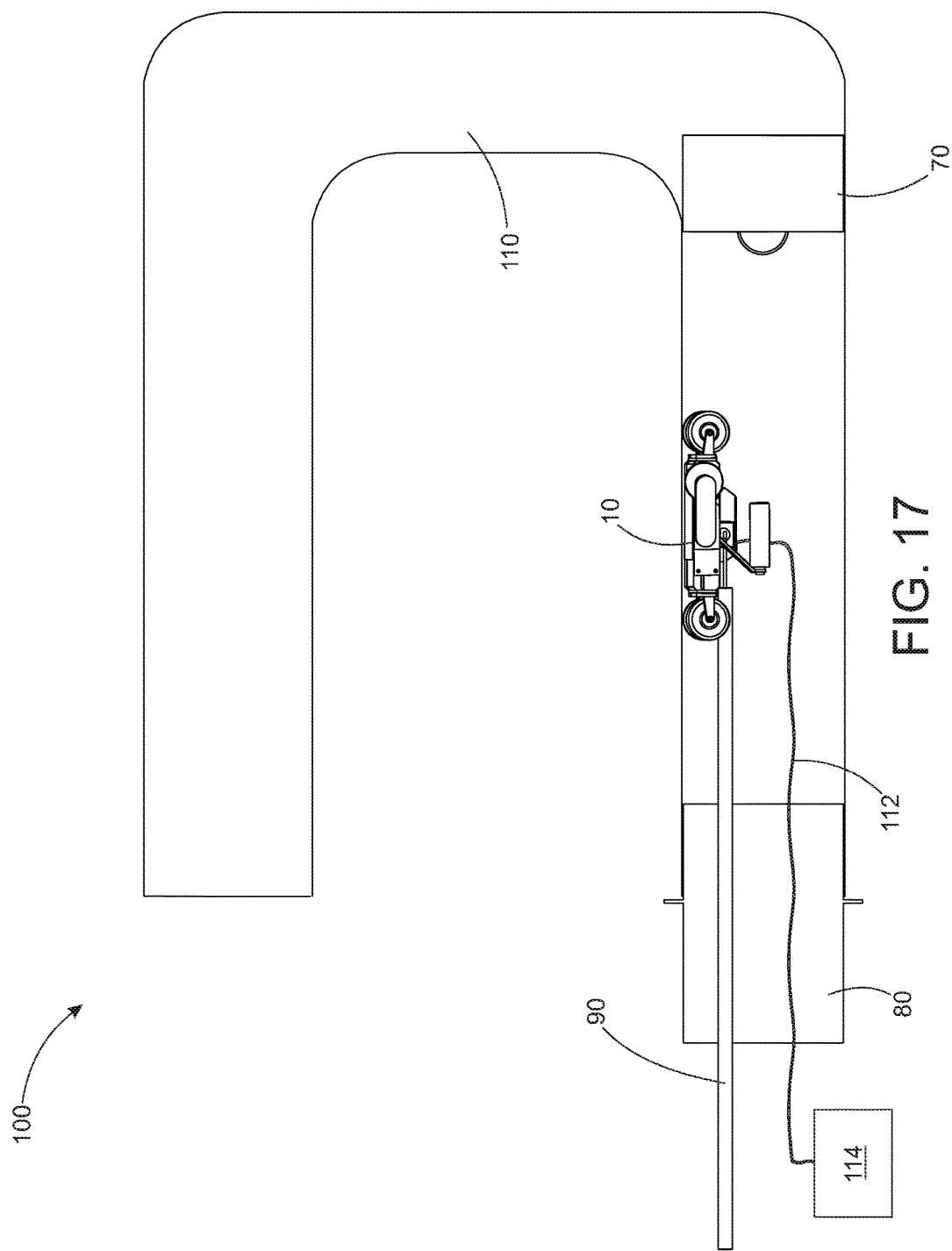
FIG. 17 is a cross section of a fire tube with a plug, collar and scanner in place for scanning a fire tube.

FIG. 17 is a cutaway view of a system for scanning a fire tube 100. The system 100 includes fire tube 110, which as discussed previously, is a U-shaped cylindrical pipe or tube that is located in a heater treater. The outside of fire tube 110 is typically submersed in a salt water oil mixture.

Plug 70 is located at the end of the section of the fire tube 110 which is to be scanned. Plug 70 is pushed down the fire tube 110 until it abuts the end of the fire tube 110 or until it is located at the bend in the fire tube 110. Plug 70 prevents the scanner 10 from travelling into the bottom section of the U and becoming stuck.

After plug 70 is placed in the fire tube 110, collar 80 is inserted into the open end of the fire tube 110. Collar 80 is sized with a diameter similar to and just smaller than fire tube 110. Collar 80 is inserted into the fire tube 110 until the flange on the collar 80 abuts the open end of the fire tube 110 preventing the collar 80 from sliding farther into the fire tube 110.

In order to begin scanning the fire tube, scanner 10 is placed in the collar 80. Hook 90 is inserted into the hook opening 46 (see FIG. 1) on the scanner 10. Cable 112 is also connected to the scanner 10 at port 28 (see FIG. 1). The other end of cable 112 is connected to computer 114.

Scanner 10 can then be rolled back and forth within the fire tube 110. The magnets 50 on scanner 10 secure the scanner 10 to the interior surface of the fire tube 110, allowing the scanner 10 to scan the entire circumference of the fire tube 110 piece by piece.

In scanning the fire tube 110, the scanner 10 is rolled back and forth in the fire tube 110 through use of the hook 90.

Figure 18:
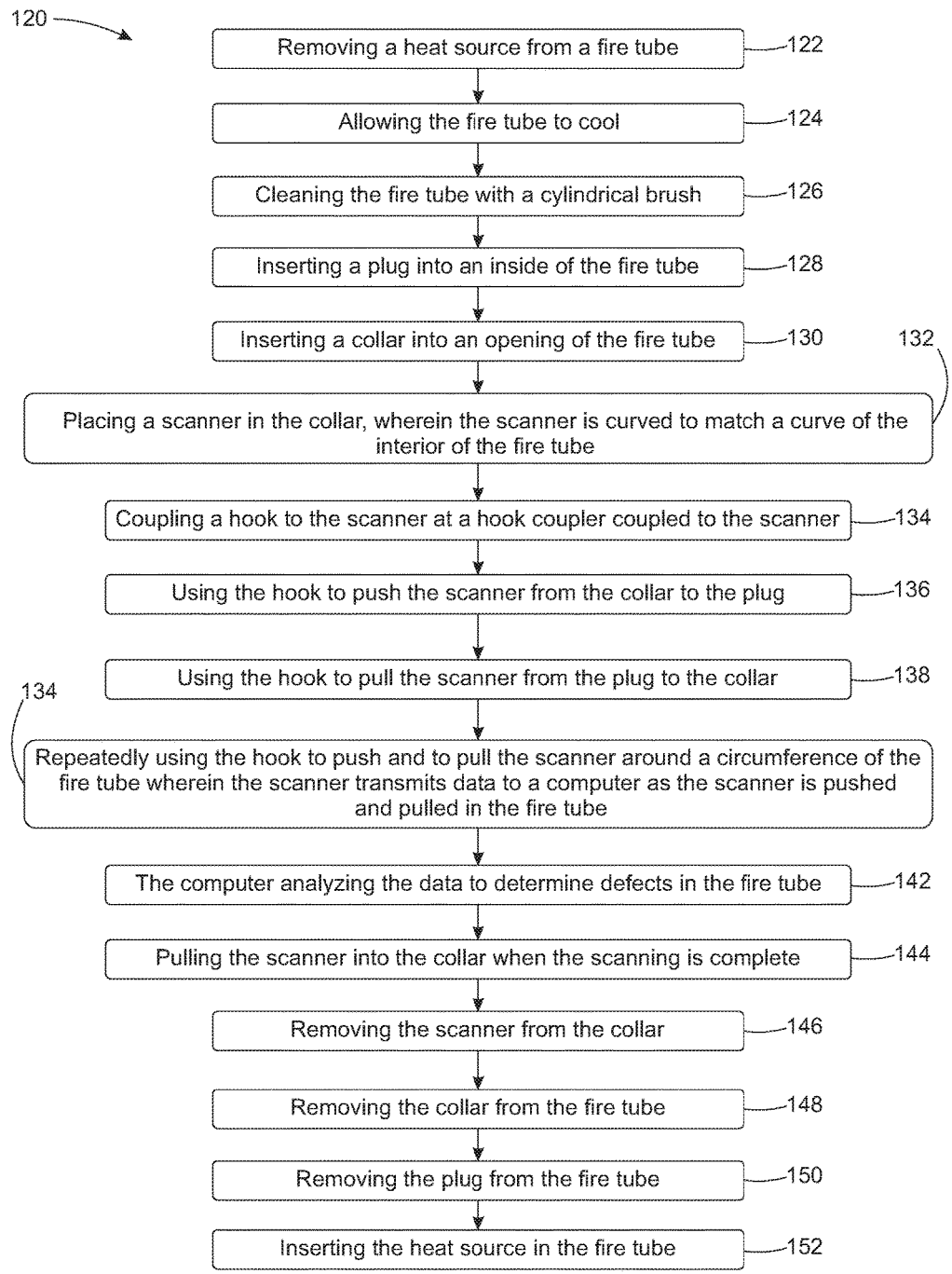
FIG. 18 is a flow chart illustrating a method of scanning a fire tube.

FIG. 18 illustrates a flow chart of a method 120 for scanning a fire tube using the scanner previously discussed.

The first step in scanning a fire tube according to this method 120 is to remove the heat source from the fire tube 122 so that the user can access the interior of the fire tube.

After heat source has been turned off and either before or after the heat source is removed from the fire tube, the fire tube is allowed to cool 124 before the scanning process. The temperature is measured in said fire tube 122 prior to scanning.

The fire tube is then cleaned with a cylindrical brush 126 or other device in order to remove as much soot and other loose material.

Once the fire tube has been cleaned, the plug is inserted into the inside of the fire tube 128. The plug is pushed back into the fire tube using a hook or other device. The plug is positioned so that it blocks the turn in the fire tube and prevents the scanner from accidentally becoming lost around the corner of the fire tube.

A collar is then inserted into the opening of the fire tube 130. The collar is a cylindrical pipe that is fit into the opening of the fire tube. The collar is inserted until a flange coupled to the outside of the collar abuts the entrance to the fire tube.

The scanner may then be placed in the collar 132. The scanner is curved to match the curve of the interior of the fire tube.

A hook is coupled to the scanner at a hook coupler on the scanner 134. The hook is a cylindrical rod with a hook located at the top. The hook is inserted into an opening on the hook coupler.

A cable is also coupled to the scanner. The cable is coupled to the scanner at a port on the data transmitters. The cable transmits data to a computer and power to the sensors on the scanner.

The hook is then used to push the scanner off of the collar, along the fire tube to the plug 136. The scanner scans the fire tube as it is pushed along the surface of the fire tube. Additionally, the distance measurer tracks the distance the scanner has travelled. The data is transmitted back to the computer.

The data may be transmitted to the computer as the fire tube is scanned or it may be stored and transmitted to the computer after the fire tube scan is complete.

The hook is then used to pull the scanner from the plug to back to the edge of the collar 138.

The scanner is then repeatedly pushed and pulled back and forth along the fire tube 140. Between each time the scanner is pushed, the scanner is rotated to a position adjacent its last position. Once the scanner has been rotated around the entire circumference of the fire tube, the fire tube scan is complete.

Data from the scan of the fire tube is transmitted to a computer and the computer analyzes the date to determine the defects in the fire tube 142. The computer may determine the depth and location of defects and the percentage of deterioration of the fire tube materials.

Once the scan is complete, the scanner is pulled back into the collar 144 in order to allow the scanner to be removed from the fire tube.

The hook may be removed from the scanner and the scanner may be removed from the collar 146.

The collar may then be removed from the fire tube 148. The plug may also be removed 150.

If the fire tube is intact enough to remain in use, then the heat source may be reinserted into the fire tube 152.

Accordingly, for the exemplary purposes of this disclosure, the components defining any embodiment of the invention may be formed as one piece if it is possible for the components to still serve their function. The components may also be composed of any of many different types of materials or combinations thereof that can readily be formed into shaped objects provided that the components selected are consistent with the intended mechanical operation of the invention. For example, the components may be formed of rubbers synthetic and/or natural, woods, glasses, composites such as fiberglass, carbon-fiber and/or other like materials, polymers such as plastic, polycarbonate, PVC plastic, ABS plastic, polystyrene, polypropylene, acrylic, nylon, phenolic, any combination thereof, and/or other like materials, metals, such as zinc, magnesium, titanium, copper, iron, steel, stainless steel, any combination thereof, and/or other like materials, alloys, such as aluminum, and/or other like materials, any other suitable material, and/or any combination thereof.

The embodiments and examples set forth herein were presented in order to best explain the present invention and its practical applications and to thereby enable those of ordinary skill in the art to make and use the invention. However, those of ordinary skill in the art will recognize that the foregoing description and examples have been presented for the purposes of illustration and example only. The description as set forth is not intended to be exhaustive or to limit the invention to the precise form disclosed. Many modifications and variations are possible in light of the teachings above without departing from the spirit and scope of the forthcoming claims. Accordingly, any components of the present invention indicated in the drawings or herein are given as an example of possible components and not as a limitation.

What is claimed is:
1. A scanner for use in scanning a fire tube in a heater treater, said scanner comprising:

a curved body, wherein said curved body comprises an outside of a curve and an inside of a curve;

at least one front edge magnet coupled to a front edge and at least one back edge magnet coupled to a back edge of said outside of said curve of said curved body;

at least one sensor coupled between the at least one front edge magnet and the at least one back edge magnet;

a sensor cover coupled to the curved body, wherein the at least one sensor is located below the sensor cover;

a data transmitter coupled to said at least one sensor;

at least one set of wheels, each set of wheels coupled to opposing edges of said curved body, each set of wheels coupled adjacent said at least one magnet;

a distance measurer coupled to said curved body;

a hook coupler coupled to said curved body; and at least one handle coupled to said inside of said curve of said curved body.

2. The scanner of claim 1, wherein the at least one handle is coupled to a handle arm.

3. The scanner of claim 1, wherein the at least one outside magnet comprises a plurality of outside magnets.

4. The scanner of claim 1, further comprising at least one port coupled to said data transmitter.

5. A system comprising a fire tube and a scanner, wherein the scanner comprises:

a body curved to fit inside the fire tube, said body having an outside of a curve and an inside of a curve;

at least one front edge magnet coupled to a front edge and at least one back edge magnet coupled to a back edge of said outside of said curve of said curved body;

at least two sensors, each sensor coupled between the at least one front edge magnet and the at least one back edge magnet;

a sensor cover coupled to the curved body, wherein the at least two sensors are located below the sensor cover, the sensor cover operating as a skid plate to protect the at least two sensors from damage during scanning;

at least two sets of wheels, each set of wheels coupled to opposing edges of said body, each set of wheels coupled adjacent each magnet;

at least one data transmitter coupled to said body; and a pole coupled to said body configured to manipulate the scanner; and wherein the fire tube comprises:

a hollow cylindrical pipe having an inside surface and an outside surface;

said outside surface of said hollow cylindrical pipe being submerged in fluid;

wherein said hollow cylindrical pipe is U shaped; and wherein said at least one magnet couples said scanner to said inside surface of said hollow cylindrical pipe.

6. The system of claim 5, wherein said at least two sets of wheels allows said scanner to be pushed along said inside surface of said hollow cylindrical pipe.

7. The system of claim 5, wherein said at least two sensors senses leakage in a magnetic field created by said at least one magnet.

8. The system of claim 5, wherein said pole is configured to push said scanner along the interior surface of said hollow cylindrical pipe.

9. The system of claim 5, wherein said data transmitter transmits data to a computer which displays said data to a user.

10. The system of claim 9, wherein said data transmitter transmits data to a computer through at least one cable.

11. The system of claim 5, wherein said scanner further comprises at least one handle.

12. The system of claim 5, wherein said scanner further comprises a distance measurer.

13. A method of scanning a fire tube for corrosion, said method comprising:

cleaning an inside of the fire tube;

placing a scanner in said fire tube, wherein said scanner is curved to match a curve of said inside of said fire tube, and wherein said scanner comprises an outside of a curve and an inside of a curve, at least one front edge magnet coupled to a front edge and at least one back edge magnet coupled to a back edge of said outside of said curve of said curved scanner, and at least one sensor coupled between the at least one front edge magnet and the at least one back edge magnet;

maintaining wheels of the scanner in contact with the fire tube by use of at least one magnet, through all orientations of the scanner within said fire tube, said at least one magnet also creating a magnetic field through said fire tube;

manually pushing and pulling said scanner along a length of said fire tube at intervals around an interior circumference of said fire tube, and sensing leakage of said magnetic field;

wherein said scanner scans the fire tube outside from a scanner location inside the fire tube looking for pits, corrosion and/or defects and transmits data on the pits, corrosion and/or defects to a computer as said scanner is pushed and pulled in said fire tube, comprising sensed leakage of said magnetic field;

said computer analyzing said data to determine defects in said fire tube; and removing said scanner from said inside of said fire tube.

14. The method of scanning a fire tube of claim 13, further comprising a distance measurer measuring a distance said scanner travels.

15. The method of scanning a fire tube of claim 14, wherein said distance is transmitted to said computer.

16. The method of scanning a fire tube of claim 13, wherein the at least one front edge magnet and the at least one back edge magnet on said scanner creates a magnetic field through said fire tube.

17. The method of scanning a fire tube of claim 16, further comprising a sensor on said scanner sensing leakage of said magnetic field.

18. The method of scanning a fire tube of claim 13, inserting a plug into said inside of said fire tube.

19. The method of scanning a fire tube of claim 13, wherein said data is transmitted to said computer by at least one cable.

20. The method of scanning a fire tube of claim 13, further comprising measuring a temperature in said fire tube prior to scanning.

* * * * *